United States Patent
Chung et al.

(10) Patent No.: US 12,162,883 B2
(45) Date of Patent: Dec. 10, 2024

(54) PROCESS FOR THE PREPARATION OF INTERMEDIATES USEFUL FOR MAKING (2S,5R)-7-OXO-N-PIPERIDIN-4-YL-6-(SULFOXY)-1,6-DIAZABICYCLO[3.2.1]OCTANE-2-CARBOXAMIDE

(71) Applicants: Merck Sharp & Dohme LLC, Rahway, NJ (US); Merck Sharp & Dohme (UK) Limited, London (GB)

(72) Inventors: John Y. L. Chung, Staten Island, NY (US); Tetsuji Itoh, Somerset, NJ (US); Jungchul Kim, Basking Ridge, NJ (US); Jacob Henry Waldman, Metuchen, NJ (US); Debra J. Wallace, Lexington, MA (US); Andrew Wood, Brookline, MA (US); Feng Xu, Staten Island, NY (US); Andrew Gibson, Welwyn Garden City (GB); Jeremy Peter Scott, Hertford (GB)

(73) Assignees: Merck Sharp & Dohme LLC, Rahway, NJ (US); Merck Sharp & Dohme (UK), London (GB)

( * ) Notice: Subject to any disclaimer, the term of this patent is extended or adjusted under 35 U.S.C. 154(b) by 665 days.

(21) Appl. No.: 17/604,525

(22) PCT Filed: Apr. 21, 2020

(86) PCT No.: PCT/US2020/029044
§ 371 (c)(1),
(2) Date: Oct. 18, 2021

(87) PCT Pub. No.: WO2020/219405
PCT Pub. Date: Oct. 29, 2020

(65) Prior Publication Data
US 2022/0194941 A1  Jun. 23, 2022

Related U.S. Application Data

(60) Provisional application No. 62/838,987, filed on Apr. 26, 2019.

(51) Int. Cl.
*C07D 471/08* (2006.01)
*C07D 211/96* (2006.01)

(52) U.S. Cl.
CPC .......... *C07D 471/08* (2013.01); *C07D 211/96* (2013.01)

(58) Field of Classification Search
CPC .................................................... C07D 471/08
USPC ........................................................ 544/349
See application file for complete search history.

(56) References Cited

U.S. PATENT DOCUMENTS

| | | | |
|---|---|---|---|
| 8,487,093 B2 | 7/2013 | Blizzard et al. | |
| 8,569,340 B2 * | 10/2013 | Hong ................... | C07D 401/12 546/187 |
| 9,604,985 B2 | 3/2017 | Miller et al. | |
| 2011/0294777 A1 | 12/2011 | Blizzard et al. | |
| 2012/0053350 A1 | 3/2012 | Mangion et al. | |
| 2013/0012712 A1 | 1/2013 | Priour et al. | |
| 2016/0122359 A1 | 5/2016 | Miller et al. | |
| 2019/0022102 A1 | 1/2019 | Gordon et al. | |
| 2019/0055216 A1 | 2/2019 | Dumas et al. | |

FOREIGN PATENT DOCUMENTS

| | | |
|---|---|---|
| WO | 2009091856 A2 | 7/2009 |
| WO | 2010126820 A2 | 11/2010 |
| WO | 201400786 A1 | 12/2014 |
| WO | 2016089718 A1 | 6/2016 |
| WO | 2016116788 A1 | 7/2016 |
| WO | 2017136254 A1 | 8/2017 |
| WO | 2018053057 A2 | 3/2018 |

OTHER PUBLICATIONS

Miller, Steven P. et al., Practical and Cost-Effective Manufacturing Route for the Synthesis of a Beta-Lactamase Inhibitor, Org. Lett., 2014, 174-177, 16.
Badland, Matthew et al., A comparative study of amide-bond forming reagents in aqueous media—Substrate scope and reagent compatibility, Tetrahedron Letters, 2017, 4391-4394, 58.
Mangion, Ian K., A concise synthesis of a beta-lactarnase Inhibitor, Organic Letters, 2011, 5480-5483, 13(20).

* cited by examiner

*Primary Examiner* — Niloofar Rahmani
(74) *Attorney, Agent, or Firm* — Patricia A. Shatynski; John C. Todaro

(57) ABSTRACT

The invention is related to the preparation of protected piperidine carboxylates suitable for use as intermediates that lead, via a series of additional process steps, including a sulfation of a hydroxy urea compound, to the preparation of the beta lactamase inhibitor (2S,5R)-7-oxo-N-piperidin-4-yl-6-(sulfoxy)-1,6-diazabicyclo[3.2.1]octane-2-carboxamide.

13 Claims, 1 Drawing Sheet

Sulfation with $SO_3$–TEA vs. Sulfation with $SO_3$–Py
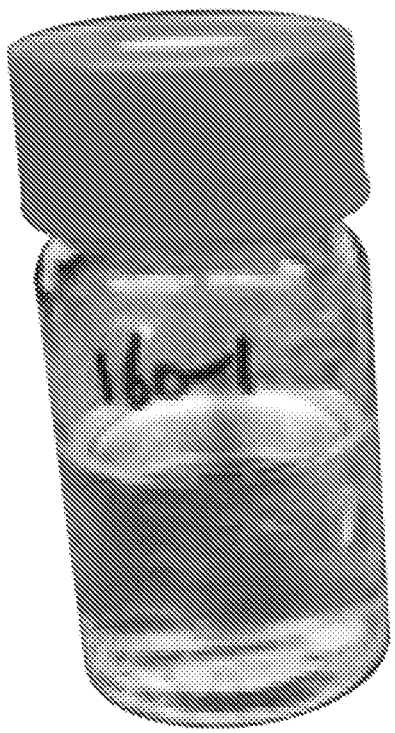 
With $SO_3$–TEA Complex  With $SO_3$–Py Complex
Use of $SO_3$–TEA complex resulted in a solution (see vial on left).
Use of $SO_3$–PY resulted in a thick slurry (the reaction vessel is positioned upside down to show the thickness effect of the slurry in the vial shown on the right)

PROCESS FOR THE PREPARATION OF INTERMEDIATES USEFUL FOR MAKING (2S,5R)-7-OXO-N-PIPERIDIN-4-YL-6-(SULFOXY)-1,6-DIAZABICYCLO[3.2.1]OCTANE-2-CARBOXAMIDE

FIELD OF THE INVENTION

The invention is related to the preparation of piperidine carboxylates suitable for use as intermediates that lead, via a series of additional process steps, to the preparation of the beta lactamase inhibitor (2S,5R)-7-oxo-N-piperidin-4-yl-6-(sulfoxy)-1,6-diazabicyclo[3.2.1]octane-2-carboxamide. This compound is a potent inhibitor of β-lactamases and is useful as effective treatment of bacterial infections when used in conjunction with β-lactam antibiotics. It is desirable to develop short, scalable, and cost effective synthesis routes for the compound.

One aspect of the invention relates to the preparation of protected piperidine carboxylates, including, tert-butyl 4-((2S,5S)-1-((nitrophenyl)sulfonyl)-5-(((nitrophenyl)sulfonyl)oxy)piperidine-2-carboxamido)piperidine-1-carboxylate. Another aspect of this invention relates to surprising and unexpected improvements directed to the sulfation of tert-butyl 4-((1R,2S,5R)-6-hydroxy-7-oxo-1,6-diazabicyclo[3.2.1]octane-2-carboxamido)piperidine-1-carboxylate which is an additional process step in the preparation of the beta lactamase inhibitor (2S,5R)-7-oxo-N-piperidin-4-yl-6-(sulfoxy)-1,6-diazabicyclo[3.2.1]octane-2-carboxamide.

BACKGROUND OF THE INVENTION

Certain 7-oxo-1,6-diazabicyclo[3.2.1]octane-2-carboxamides are inhibitors of β-lactamase and, when used in conjunction with β-lactam antibiotics, can be effective for the treatment of bacterial infections. See, for example, U.S. Pat. No. 8,487,093 which discloses 7-oxo-1,6-diazabicyclo[3.2.1]octane-2-carboxamides such as (2S,5R)-7-oxo-N-piperidin-4-yl-6-(sulfoxy)-1,6-diazabicyclo[3.2.1]octane-2-carboxamide and its synthesis from a ketosulfoxonium ylide intermediate containing an amide side chain, where the ylide intermediate is cyclized to a 5-oxo-piperidine-2-carboxamide using an Ir, Rh, or Ru catalyst.

U.S. Pat. No. 9,604,985 discloses a process for the preparation of N-protected 6-(piperidine-4-ylcarbamoyl)piperidin-3-yl sulfonates which comprises forming a lactone by contacting a (2S,5S)-5-hydroxypiperidine-2-carboxylic acid derivative with a protecting group agent such as 2-nitrobenzene-1-sulfonyl chloride, in the presence of an aqueous base. The lactone is further contacted with an azacycloalkylamine followed by contact with a sulfonyl halide in the presence of a tertiary amine base.

U.S. Pat. No. 9,604,985 specifically exemplifies an involved 4 step process for making an intermediate, tert-butyl 4-((2S,5S)-1-((2-nitrophenyl)sulfonyl)-5-(((2-nitrophenyl)sulfonyl)oxy)piperidine-2-carboxamido)piperidine-1-carboxylate

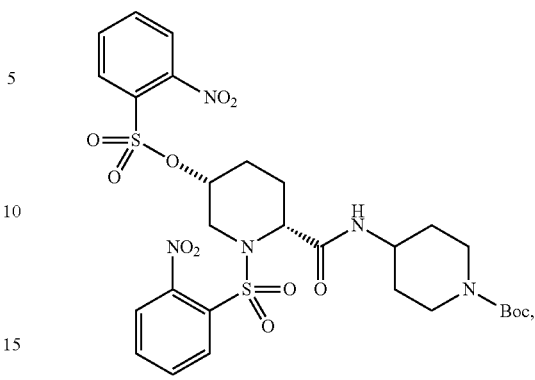

(Ia)

by reacting (2S,5S)-5-hydroxypiperidine-2-carboxylic acid with 2-nitrobenzenesulfonyl chloride in the presence of trimethylamine to form lactone, (1S,4S)-5-((2-nitrophenyl)sulfonyl)-2-oxa-5-azabixyclo[2.2.2]octan-3-one. The lactone is then contacted with an azacycloalkylamine having a protecting group, such as, for example Boc (tert-butyloxycarbonyl). The reaction product is then contacted with a sulfonyl halide in the presence 4-dimethylaminopyridine to form tert-butyl 4-((2S,5S)-1-((2-nitrophenyl)sulfonyl)-5-(((2-nitrophenyl)sulfonyl)oxy)piperidine-2-carboxamido)piperidine-1-carboxylate.

Additional embodiments disclosed in U.S. Pat. No. 9,604,985 add a series of process steps that ultimately lead to the synthesis of various 7-oxo-1,6-diazabicyclo[3.2.1]octanes, among them, (2S,5R)-7-oxo-N-piperidin-4-yl-6-(sulfoxy)-1,6-diazabicyclo[3.2.1]octane-2-carboxamide, suitable for use as β-lactamase inhibitors. One such process step, identified as Step F in U.S. Pat. No. 9,604,985, is a sulfation where a hydroxide compound of the following structure:

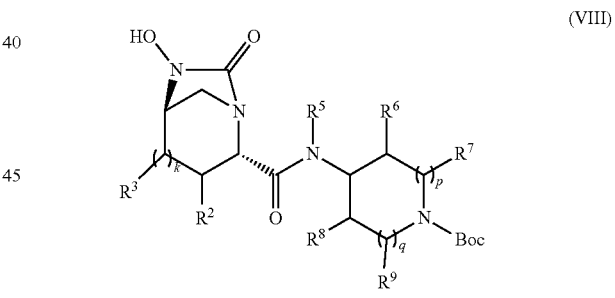

(VIII)

is contacted with a sulfating agent in the presence of an organic base to form the sulfonated compound:

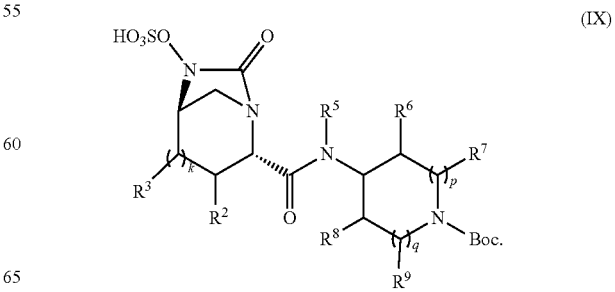

(IX)

The sulfating agent in Step F is suitably a complex of sulfur trioxide and an amine, wherein the amine is suitably a tertiary amine including, for example, acyclic amines (e.g., trimethylamine), TEA, DIPEA, dimethylphenylamine, and dimethylbenzylamine), cyclic amines (e.g., 1-methylpyrrolidine and 1-methylpiperidine) and aromatic amines having one or more N atoms as part of the aromatic ring (e.g., 1-methylimidazole, pyridine, and pyrimidine). Halosulfonic acids (e.g., chlorosulfonic acid) and tertiary amide complexes of $SO_3$ (e.g., $DMF-SO_3$) are also suitable sulfating agents. A class of suitable sulfating agents consists of complexes of each of the following amines with sulfur trioxide: pyridine, trimethylamine, and triethylamine. Another class of suitable sulfating agents consists of pyridine-$SO_3$ complex, $DMF-SO_3$ complex and chlorosulfonic acid. The sulfating reagent is typically employed in an amount in a range of from about 1.5 to about 7.0 equivalents per equivalent of the hydroxy urea compound VIII mentioned above.

The required organic base is suitably pyridine or a tertiary amine such as 2-picoline, 2,6-lutidine, an individual trimethylpyridine, or a mixture of two or more trimethylpyridines. A class of suitable bases consists of picoline (e.g., 2-picoline), 2,6-lutidine and 2,4,6-trimethylpyridine. U.S. Pat. No. 9,604,985 discloses that the preferred base is 2-picoline or pyridine. The base is typically employed in an amount in a range of from about 1 to about 3 equivalents per equivalent to the above-mentioned hydroxy urea compound.

S.P. Miller et al. discusses the optimization of the synthesis for (2S,5R)-7-oxo-N-piperidin-4-yl-6-(sulfoxy)-1,6-diazabicyclo[3.2.1]octane-2-carboxamide taught by the U.S. Pat. No. 9,604,985 in detail. (See S. P Miller et al., "Practical and Cost-Effective Manufacturing Route for the Synthesis of a β-Lactamase Inhibitor", Org. Lett. 2014, 16, 174-177). In the end, the route describe in both S. P. Miller et al. and U.S. Pat. No. 9,604,985 contains a cumbersome four step process requiring use of two protecting groups in order to form, tert-butyl 4-((2S,5S)-1-((2-nitrophenyl)sulfonyl)-5-(((nitrophenyl)sulfonyl)oxy)piperidine-2-carboxamido)piperidine-1-carboxylate as an intermediate. In addition, the two references describe subsequent process steps and intermediates needed to ultimately produce the β-lactamase inhibitors of interest. One of these steps includes a sulfation of a hydroxy urea intermediate that requires the hydroxy urea intermediate to contact a sulfating agent and an organic base. (see Step F found in U.S. Pat. No. 9,604,985).

It would be beneficial to discover alternative processes that reduce or eliminate the need for cumbersome steps or excessive reagents, when possible, without incurring detrimental effects on process yields, in order to obtain more efficient and more economically viable processing methodologies.

SUMMARY OF THE INVENTION

The present invention relates to a process for preparing intermediates useful for synthesizing the β-lactamase inhibitor (2S,5R)-7-oxo-N-piperidin-4-yl-6-(sulfoxy)-1,6-diazabicyclo[3.2.1]octane-2-carboxamide.

One embodiment of the invention is an efficient two step process for preparing the compound of formula I

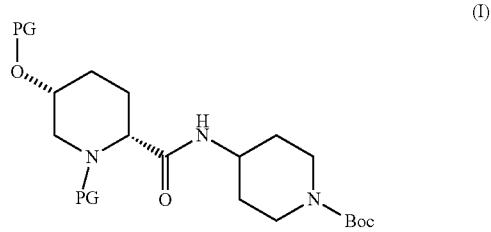

(I)

or a salt thereof comprising:
  A) coupling a pipecolic acid with an azacycloalkylamine in the presence of a first organic solvent, N-(3-dimethylaminopropyl)-N'-ethylcarbodiimide hydrochloride (EDC), 1-hydroxy-2-pyridone (HOPO), and at least one acid to form a compound of formula II

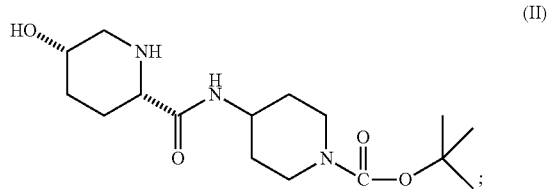

(II)

and
  B) contacting the compound of formula (II) with a protecting group in the presence of a nucleophilic catalyst and a second organic solvent to form the compound of formula (I).

The compound of formula I may be used as an intermediate in the production of β-lactamase inhibitors.

The improved two-step process eliminates the need for the formation of a lactone and the need for the use of two different protecting group steps as taught by U.S. Pat. No. 9,604,095 and S.P. Miller et al.

Another aspect of this invention relates to the unexpected and surprising discovery that elimination of a chemical reagent in the sulfation described and exemplified as step F in U.S. Pat. No. 9,604,985 can result in the production of a compound of formula (IV) or a pharmaceutically acceptable salt thereof

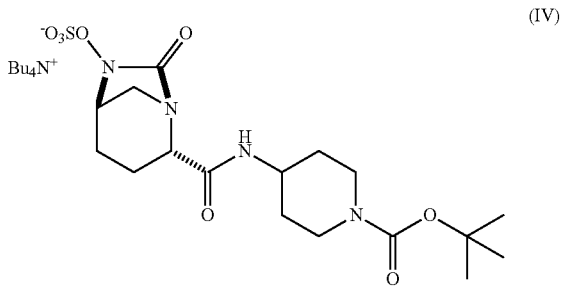

(IV)

without impacting on compound yield or reaction rate. The process of the present invention also increases the process robustness since the sulfation under the new conditions results in a homogeneous solution rather than a thick slurry.

Other embodiments, aspects and features of the present invention are either further described in or will be apparent from the ensuing description, examples, and appended claims.

BRIEF DESCRIPTION OF THE DRAWINGS

These and other features of the invention will become clearer from the detailed description below as well as the drawing, in which:

FIG. 1 shows the differences in the sulfation step reaction mixtures when utilizing different SO₃ amine complexes, specifically, use of a SO₃-TEA complex versus a SO₃-Py (SO₃-pyridine) complex.

DETAILED DESCRIPTION OF THE INVENTION

The present invention relates to a process for preparing a compound of Formula I via the coupling of pipecolic acid with an azacycloalkylamine to form an intermediate utilized in a process to make the beta lactamase inhibitor (2S,5R)-7-oxo-N-piperidin-4-yl-6-(sulfoxy)-1,6-diazabicyclo[3.2.1]octane-2-carboxamide.

As was mentioned previously, the improved process of the present invention, provides for a two-step synthesis for the compound of formula I versus the four step process disclosed in U.S. Pat. No. 9,604,095 and S. P. Miller et al. The process of the present invention eliminates the need for the formation of a lactone and the need for the use of two different protecting group steps as required by U.S. Pat. No. 9,604,095 and S. P. Miller et al. In the process of the present invention the protecting group (for example, nitrobenzenesulfonyl chloride) is utilized only once and installed in one step in contrast with its two-time utilization in the process described in Miller et al. and U.S. Pat. No. 9,604,095 since the lactone formation step is no longer required.

One embodiment of the invention is a process of preparing a compound of Formula I thereof

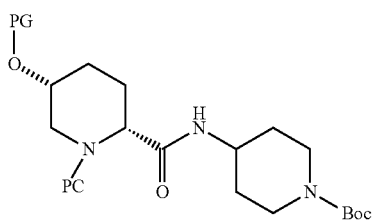

comprising:
A) coupling a pipecolic acid with an azacycloalkylamine in the presence of a first organic solvent, N-(3-dimethylaminopropyl)-N'-ethylcarbodiimide hydrochloride (EDC), 1-hydroxy-2-pyridone (HOPO), and at least one acid to form a compound of formula II

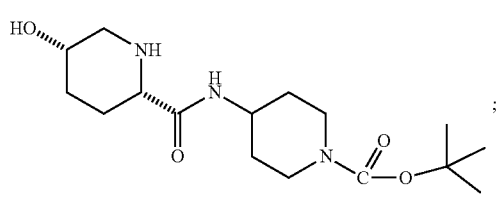

and
B) contacting the compound of formula (II) with a protecting group in the presence of a nucleophilic catalyst and a second organic solvent to form the compound of formula I.

In one embodiment of the invention, in step A) the pipecolic acid is

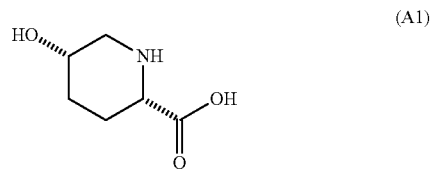

and the azacycloalkylamine is

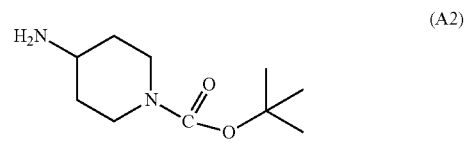

and the at least one acid is selected from aqueous hydrochloric acid or methanesulfonic acid (MsOH).

In another embodiment of the invention, the first organic solvent may be any suitable organic solvent, i.e., one in which the reactants are soluble or partically soluble. Suitable organic solvents include, but are not limited to, DCM, DMF, AcNMe₂ (N,N-dimethylacetamide), THF, MeTHF (2-methyltetrahydrofuran), EtOAc, i-PrOAc (isopropyl acetate), acetonitrile and mixtures thereof. A preferred solvent is acetonitrile.

In another embodiment of the invention, the second organic solvent may be any suitable organic solvent, i.e., one in which the reactants are soluble or partically soluble. Suitable organic solvents include, but are not limited to, DCM, DMF, AcNMe₂ (N,N-dimethylacetamide), THF, MeTHF (2-methyltetrahydrofuran), EtOAc, i-PrOAc (isopropyl acetate), acetonitrile and mixtures thereof. A preferred solvent is acetonitrile.

In another embodiment of the invention, step B), the a nucleophilic catalyst is 4-dimethylaminopyridine (DMAP) and an organic solvent is acetonitrile (MeCN).

In one embodiment of the invention, the protecting group is a sulfonyl group generated from sulfonyl halides such as methanesulfonyl chloride, chloromethanesulfonyl chloride, dicloromethanesulfonyl chloride, benzenesulfonyl chloride, p-trifluromethylbenzenesulfonyl chloride, p-toluenesulfonyl chloride, p-bromobenzenesulfonyl chloride, p-fluorobenzenesulfonyl chloride, p-methoxybenzenesulfonyl chloride, 2-nitrobenzenesulfonyl chloride, 4-nitrobenzenesulfonyl chloride, 2,4-dichlorobenzenesulfonyl chloride, and p-trifluoromethylbenzenesulfonyl chloride.

In another embodiment of the invention, the protecting group is chosen from chloromethanesulfonyl chloride, p-trifluromethylbenzenesulfonyl chloride, p-bromobenzenesulfonyl chloride, 2-nitrobenzenesulfonyl chloride, 4-nitrobenzenesulfonyl chloride and 2,4-dichlorobenzenesulfonyl chloride.

In one embodiment of the invention, the protecting group is chosen from 2-nitrobenzenesulfonyl chloride, 4-nitrobenzenesulfonyl chloride and mixtures thereof. In a variant of this embodiment, the nitrobenzenesulfonyl chloride is 2-nitrobenzenesulfonyl chloride (2-NsCl). In yet another embodiment, the nitrobenzenesulfonyl is 4-nitrobenzenesulfonyl (4-NsCl).

In one embodiment of the process of the invention, in step A) of process for synthesis of a compound of formula (I) or a salt thereof, the coupling comprises the following steps:

1) adding the azacycloalkylamine of Formula (A2) to acetonitrile to form a mixture, 2) adding at least one acid selected from aqueous hydrochloric acid or MsOH to the mixture of step 1;

3) adding HOPO and the pipecolic acid of Formula (A1) to the mixture of step 2 and then heating the mixture to a temperature between about 20° C. to about 50° C.; and 4) adding EDC to the heated mixture of step 3.

In another aspect of the invention, the at least one acid is aqueous hydrochloric acid. In another aspect of the invention, the at least one acid is methanesulfonic acid (MsOH).

In one embodiment of the invention the temperature ranges from between about 20° C. to about 50° C. In one aspect of this embodiment, the temperature is about 40° C.

In one aspect the aqueous hydrochloric acid concentration ranges from about 6N to concentrated HCl (37 wt %). In one embodiment of the invention, concentrated HCl (37 wt %) is utilized.

Another aspect of the invention relates to the unexpected and surprising improvement to the general sulfation step, Step F, described in U.S. Pat. No. 9,604,985 to Miller et al. ("the '985 patent"). As mentioned previously, Step F of the '985 patent requires that the sulfation of a hydroxy urea compound with a sulfating agent in the presence of an organic base such as pyridine, 2-picoline, 2,6-lutidine, or trimethylpyridines. The present inventors have found that the elimination of the organic base and the use of a proper SO₃ amine complex results in a more homogenous mixture than the heterogenous mixture that results when the organic base and pyridine SO₃ complex are present.

One aspect of the invention relates to a process for preparing a compound of Formula IV:

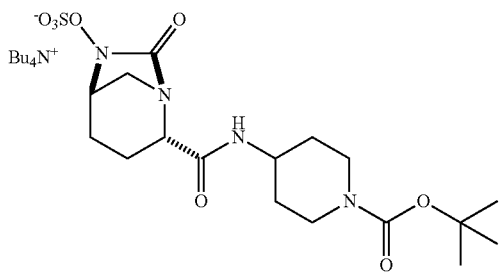

comprising:
contacting a hydroxy urea of formula (III);

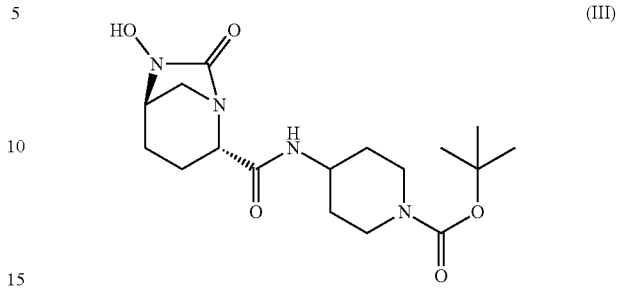

in the presence of a sulfur trioxide amine selected from sulfur trioxide-triethyl amine, sulfur trioxide-tripropyl amine, and sulfur trioxide-tributylamine, and at least one solvent selected from 2-methyltetrahydrofuran and tetrahydrofuran to form a reaction mixture; adding an aqueous solution of dipotassium phosphate to the reaction mixture; and adding tetrabutylammonium hydrogensulfate to form a compound (IV) in a biphasic mixture.

The careful selection of SO₃-amine complex and solvent used in the sulfation process of the present invention produces yields of the compound of formula (VI) greater than about 90% conversion. One embodiment of the invention results in a greater than 97% within in five hours. Additionally, use of the presently disclosed SO₃-amine complex and solvent system in the sulfation of the present invention results in robust process conditions with homogenous reaction mixtures FIG. 1 illustrates the types of reaction mixtures encountered in the sulfation process described above utilizing different SO₃ amine complexes, specifically a SO₃-TEA complex and a SO₃-Py (SO₃-Pyridine) complex. As can be seen in FIG. 1, the sulfation employing the SO₃-TEA complex resulted in a homogeneous solution while the sulfation employing the use of the SO₃-Py complex and picoline resulted in a thick slurry. From a mass transport processing perspective, it is more desirable to have a homogeneous solution as it is easier to scale up.

Another embodiment of the invention is the formation of the compound of formula (V)

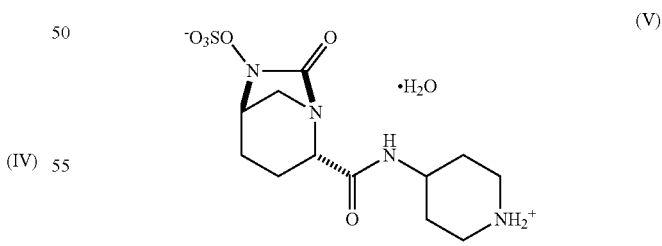

comprising:
contacting compound (IV) with trimethylsilyl bromide (TMSBr) in the presence of an organic solvent; and adding tetrabutylammonium acetate-acetic acid complex in acetonitrile and water to form compound (V).

The process for making the compound (V) further comprising adding isopropyl alcohol to the mixture containing compound (V) and filtering the resultant solution.

In one embodiment of the invention, the isopropyl alcohol is added in an range from about 4× to about 7× the volume relative to compound IV.

In one embodiment of the invention, the tetrabutylammonium acetate-acetic acid complex is present in an amount in a range of from about 0.1 to about 0.45 equivalents per equivalent of the sulfate compound of formula (IV).

In another embodiment of the invention, the organic solvent may be any suitable organic solvent, i.e., one in which the reactants are soluble. Suitable organic solvents include, but are not limited to, DCM, DMF, AcNMe2 (N,N-dimethylacetamide), THF, MeTHF (2-methyltetrahydrofuran), EtOAc, i-PrOAc (isopropyl acetate), acetonitrile and mixtures thereof. A preferred solvent is acetonitrile.

Another embodiment of the invention includes synthesis of the beta lactamase inhibitor (2S,5R)-7-oxo-N-piperidin-4-yl-6-(sulfoxy)-1,6-diazabicyclo[3.2.1]octane-2-carboxamide utilizing intermediates and process improvements of the present invention. Scheme A provides an overview of general process for making (2S,5R)-7-xo-N-piperidin-4-yl-6-(sulfoxy)-1,6-diazabicyclo[3.2.1]octane-2-carboxamide.

Scheme A

Step 1. Amidation

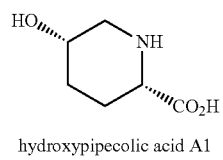

hydroxypipecolic acid A1

+

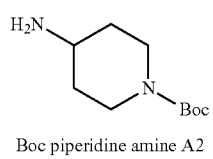

Boc piperidine amine A2

1. conc. HCl, HOPO,
EDC—HCl, MeCN
→

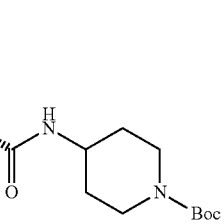

amide II

Step 2. Bis-Nosylation amide II
1. 4-NsCl,
DMAP, MeCN
→

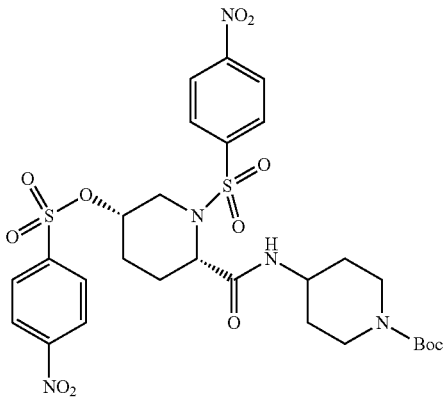

N,O-bis(nosyl) amide 4
compoud of formula
(I), where PG is 4-NsCl

Step 3. SN2 Displacment/Nosyl Deprotection

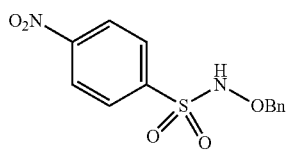

benzyloxysulfonamide 5

N,O-bis(nosyl) amide 4
1. K₂CO₃, DMAc
→

[
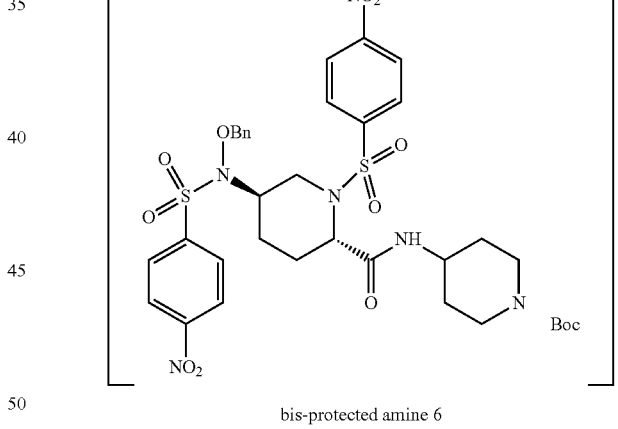

bis-protected amine 6
]

2. MeOH, thioglycolic acid,
K₂CO₃
3. aq. NaCl
4. pTSA, MeCN
↓ diamine pTSA salt 7

-continued

Step 4. Benzyl Urea Formation diamine pTSA salt 7 
1. DIPEA, Me₂SiCl₂, CDI, MeCN
2. IPA
3. HCl,
⟶

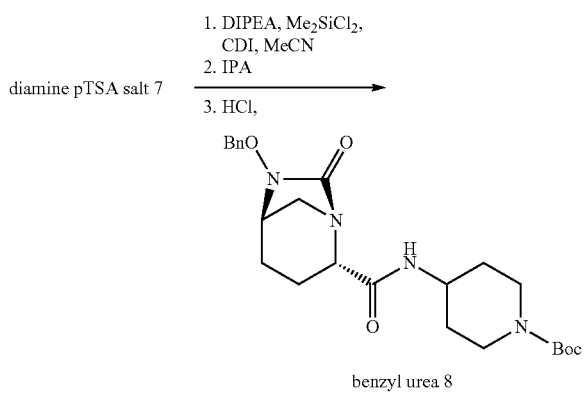

benzyl urea 8

Step 5. Hydrogenolysis benzyl urea 8 
1. H₂, Pd/C DABCO IPAc, BSA
2. HOAc, H₂O
⟶

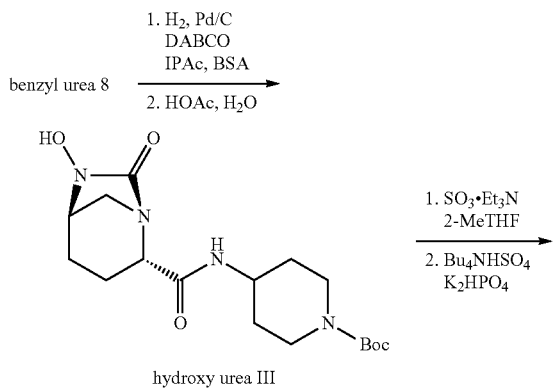

hydroxy urea III

1. SO₃·Et₃N 2-MeTHF
2. Bu₄NHSO₄ K₂HPO₄

Step 6. Sulfation

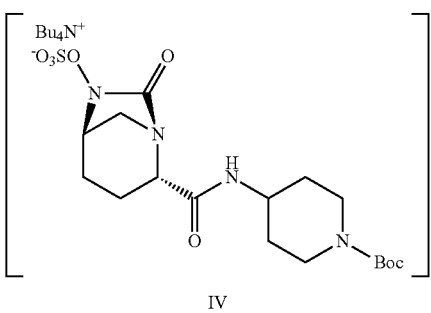

IV

Step 7. Boc Deprotection

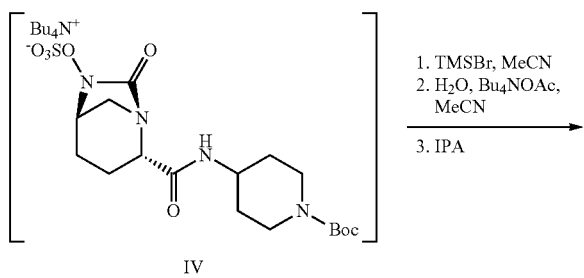

IV

1. TMSBr, MeCN
2. H₂O, Bu₄NOAc, MeCN
3. IPA
⟶

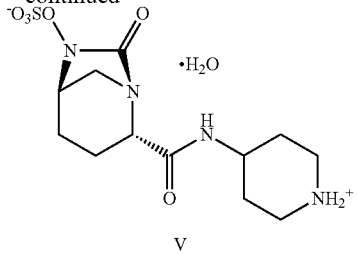

V

Compounds such as (2S,5R)-7-oxo-N-piperidin-4-yl-6-(sulfoxy)-1,6-diazabicyclo[3.2.1]octane-2-carboxamide can exhibit inhibition of β-lactamase and thus can be used as β-lactamase inhibitors in combination with β-lactam antibiotics (e.g., imipenem, ceftazidime and piperacillin) to treat bacterial infections caused by microorganisms normally resistant to s-lactam antibiotics due to the presence of the β-lactamases.

It is to be understood that the solvents, agents, catalysts, reaction amounts, reaction temperatures, etc. described above with respect to the process and its embodiments and sub-embodiments are intended only to illustrate, not limit, the scope of the process. For example, the solvent employed in any of Steps (a) to (c) can be any organic substance which under the reaction conditions employed in the step of interest is in the liquid phase, is chemically inert, and will dissolve, suspend, and/or disperse the reactants and any reagents so as to bring the reactants and reagents into contact and to permit the reaction to proceed. Similar considerations apply to the choice of bases, catalysts, and other reagents employed in the process steps. Furthermore, each of the steps can be conducted at any temperature at which the reaction forming the desired product can detectably proceed. The reactants, catalysts and reagents in a given step can be employed in any amounts which result in the formation of at least some of the desired product. Of course, a high conversion (e.g., at least about 60% and preferably higher) of starting materials in combination with a high yield (e.g., at least about 60% and preferably higher) of desired products is typically the objective in each step, and the choice of solvents, agents, catalysts, reaction amounts, temperatures, etc. that can provide relatively good conversions and yields of product are preferred, and the choices that can provide optimal conversions and yields are more preferred. The particular solvents, agents, catalysts, reaction amounts, reaction temperatures, etc. described above with respect to the process and its embodiments and sub-embodiments can provide good to optimum conversions and yields.

The reaction times for the process steps described above depend upon such factors as (i) the choice and relative proportions of the starting substrate and other reagents, (ii) the choice of solvent, (iii) the choice of reaction temperature, and (iv) the level of conversion desired. The reactions are typically conducted for a time sufficient to achieve 100% or near 100% conversion (e.g., 99.5%, 99.0%, 98.0%, 97.0% or 95%).

The progress of any reaction step set forth herein can be followed by monitoring the disappearance of a reactant and/or the appearance of the desired product using such analytical techniques as TLC, HPLC, IR, NMR or GC.

Abbreviations employed herein include the following:

| | |
|---|---|
| BLI | beta-lactamase inhibitor |
| Bn | benzyl |
| Boc | t-butyloxycarbonyl |
| Cbz | carbobenzoxy (alternatively, benzyloxycarbonyl) |
| CDI | carbonyldiimidazole |
| DCM | dichloromethane |
| DIPEA | diisopropylethylamine (or Hunig's base) |
| DMAC or DMAc | N,N-dimethylacetamide |
| DABCO | 1,4-diazabicyclo[2.2.2]octane |
| DME | 1,2-dimethoxyethane |
| DMF | N,N-dimethylformamide |
| Et | ethyl |
| EtOAc | ethyl acetate |
| GC | gas chromatography |
| HPLC | high-performance liquid chromatography |
| IPA | isopropyl alcohol |
| IPAc | isopropyl acetate |
| IR | infrared |
| LCAP | liquid chromatogram area percent |
| Me | methyl |
| MeCN | acetonitrile |
| MeOH | methanol |
| MTBE | methyl tert-butyl ether |
| 4-NMM | 4-methylmorpholine |
| NMP | N-methyl pyrrolidinone |
| NMR | nuclear magnetic resonance |
| PG | protective group |
| RB | round bottom |
| t-Bu | tert-butyl |
| TEA | triethylamine |
| TFA | trifluoroacetic acid |
| THF | tetrahydrofuran |
| TLC | thin layer chromatography |

The following example serves only to illustrate the invention and its practice. The examples are not to be construed as limitations on the scope or spirit of the invention.

Example 1

(2S,5R)-7-oxo-N-piperidin-4-yl-6-(sulfoxy)-1,6-diazabicyclo[3.2.1]octane-2-carboxamide Step 1 Amidation Tert-butyl 4-((2S,5S)-5-hydroxypiperidine-2-carboxamido)piperidine-1-carboxylate (1-c)

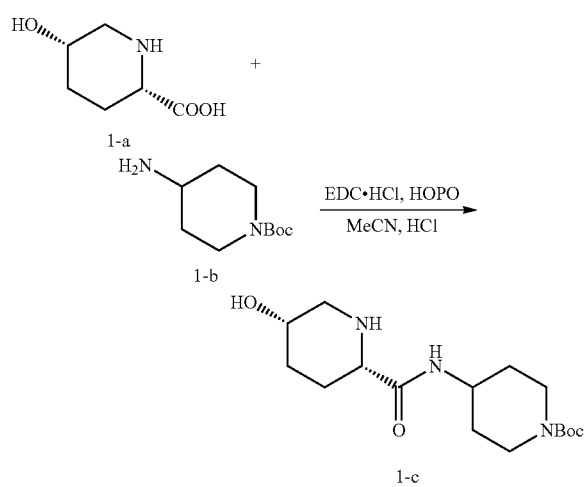

To a mixture of 4-amino-1-Boc-piperidine (1-b) (20 g, 98 wt %, 0.1 mol) in acetonitrile (400 mL) was added 37 wt % HCl (9.85 g, 0.1 mol) dropwise over 1 h. HOPO (8.3 g, 0.075 mol) and (2S,5S)-5-hydroxypiperidine-2-carboxylic acid (1-a) (16.7 g, 98 wt %, 0.115 mol) were then added. The batch was heated to 40° C. and EDC HCl (26.8 g, 0.14 mol) was added. The reaction mixture was aged for at least 5 h at 40-45° C., then cooled to 20-25° C. NaOH (5M, 140 mL) and methyl-t-butyl ether (120 mL) were added. The separated organic layer was washed 5M NaOH (40 mL×3).

The organic layer was solvent switched to acetonitrile at a final volume of ~120 mL. Methyl-t-butyl ether (180 mL) was added over 1 h. The batch was filtered and the cake was washed MTBE (100 mL×2). Vacuum oven dry at 40-45° C. gave the desired product (1-c). $^1$H NMR (500 MHz, d$_6$-DMSO) δ 7.67 (d, J=8.1 Hz, 1H), 4.48 (s, br, 1H), 3.84 (m, 2H), 3.72 (m, 1H), 3.44 (m, 1H), 3.04 (dd, J=8.6, 3.7 Hz, 1H), 2.82 (s, br, 2H), 2.63 (dd, J=13.3, 2.6 Hz, 1H), 2.57 (dd, J=13.3, 4.6 Hz, 1H), 2.17 (s, br, 1H), 1.77 (m, 1H), 1.67 (m, 2H), 1.57 (m, 1H), 1.52 (m, 1H), 1.43 (m, 1H), 1.39 (s, 9H), 1.27 (m, 2H). $^{13}$C NMR (125 MHz, d$_6$-DMSO) δ 172.0, 159.9, 78.6, 63.5, 57.5, 50.6, 45.4, 42.3 (br), 31.3 (rotamer), 31.2 (rotamer), 30.7, 28.1, 24.6. HRMS calc'd for $C_{16}H_{30}N_3O_4$ [M+H]$^+$ 328.2231; found 328.2235.

Step 2 Bis-Nosylation

Tert-butyl-4-((2S,5S)-1-((4-nitrophenyl)sulfonyl)-5-(((4-nitrophenyl)sulfonyl)oxy) piperidine-2-carboxamido)piperidine-1-carboxylate Hydrate (1-e)

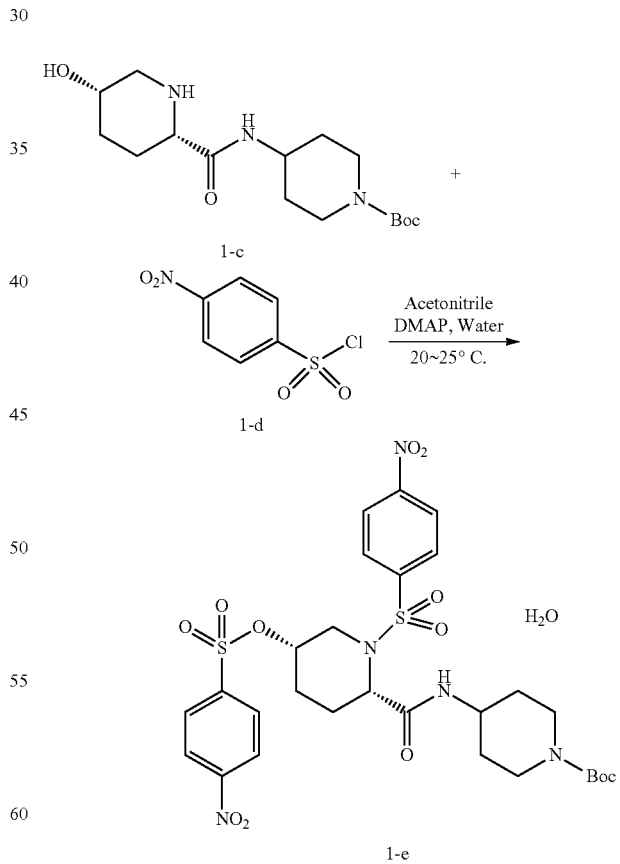

To a mixture of the amide intermediate (1-c) (33.4 g, 98 wt %, 0.1 mol) and DMAP (29.3 g, 0.24 mol) in acetonitrile (300 mL) was dropwise added a solution of 4-nitrobenzenesulfonyl chloride (1-d) (48.8 g, 0.22 mol) in acetonitrile (130 mL) at ambient temperature. The reaction was aged several hours until the reaction was complete. Water (130 mL) was then added at ambient temperature and the batch was seeded with bis-nosyl amide. Additional water (330 mL) was added over 6 h. Upon filtration, the wet cake was washed with a solution of 50% MeCN in water (270 mL). Vacuum oven dry at 40° C. afforded the desired product (1-e). $^1$H NMR (500 MHz, d$_6$-DMSO) δ 8.47 (m, 2H), 8.38 (m, 2H), 8.25 (m, 2H), 7.99 (d, J=7.5 Hz, 1H), 7.94 (m, 2H), 4.52 (m, 1H), 4.38 (d, J=5.4 Hz, 1H), 3.89 (dd, J=11.4, 5.3 Hz, 1H), 3.74 (m, 2H), 3.60 (t, J=11.4 Hz, 1H), 3.41 (m, 1H), 2.79 (s, br, 2H), 1.90 (m, 1H), 1.78 (m 1H), 1.75 (m, 1H), 1.52 (m, 3H), 1.39 (s, 9H), 1.13 (m, 2H). $^{13}$C NMR (125 MHz, d$_6$-DMSO) δ 168.1, 153.8, 150.8, 149.9, 143.9, 141.0, 129.3, 128.5, 125.1, 124.6, 78.6, 76.7, 52.7, 45.6, 45.4, 42.3 (rotamer), 41.7 (rotamer), 30.8 (br), 28.0, 26.4, 25.7. HRMS calc'd for $C_{28}H_{36}N_5O_{12}S_2$ [2M+H]$^+$1395.3520; found 1395.3560.

Step 3 Diamine pTSA Salt

A mixture of benzyloxysulfonamide (10.2 g, 33.0 mmol), K$_2$CO$_3$ (4.4 g, 31.6 mmol) in DMAc (40 mL) was agitated at 50° C. for several hours. The N,O-bis(nosyl) amide, 1-e, (20.0 g, 28.7 mmol) was then added and the reaction mixture was agitated at 55° C. until the reaction was deemed complete. MeOH (200 mL) and thioglycolic acid (11.9 g, 129.2 mmol) were added at ambient temperature. Then, K$_2$CO$_3$ (35.7 g, 258.3 mmol) was added at 0° C. The reaction mixture was stirred at 0° C. until the reaction was deemed complete. Water (200 mL) and toluene (120 mL) were added to the reaction mixture. The organic phase was separated and the aqueous layer was extracted with toluene (60 mL). The combined organic phase was washed with 5 wt % K$_2$CO$_3$ (40 mL×2) followed by 5 wt % NaCl (40 mL). The organic was concentrated in vacuum to ~100 mL at 35° C.

To a solution of diamine free base (10.0 g assay, 23.1 mmol) at 40° C. was added a solution of p-toluenesulfonic

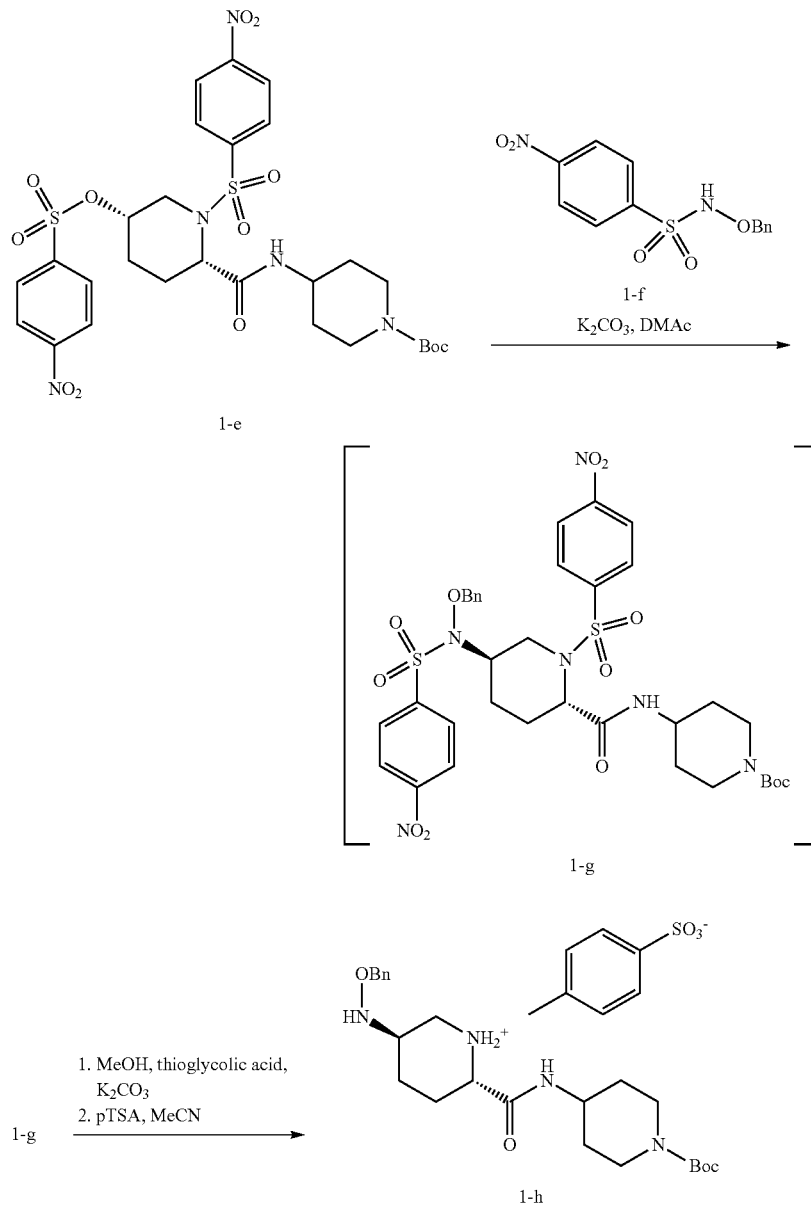

acid (4.0 g, 23.1 mmol) in MeCN (25 mL) dropwise. After ~10% of the pTSA solution in MeCN was added, the batch was seeded with diamine pTSA salt seeds. After pTSA addition, the slurry was agitated at 0° C. for several hours before filtration. The wet cake was washed with a solution of acetonitrile/toluene (1:3 v/v, 20 mL×3). Vacuum oven dry at <70° C. afforded the desired diamine pTSA salt. $^1$H NMR (500 MHz, d$_6$-DMSO) δ 8.95 (s, br, 2H), 8.37 (d, J=7.6 Hz, 1H), 7.48 (d, J=8.0 Hz, 2H), 7.33 (m, 5H), 7.11 (d, J=8.0 Hz, 2H), 6.83 (d, J=5.5 Hz, 1H), 4.58 (s, 2H), 3.79 (m, 3H), 3.64 (dd, J=12.5, 2.4 Hz, 1H), 3.34 (m, 1H), 3.15 (m, 1H), 2.89 (s, br, 2H), 2.69 (t, J=11.5 Hz, 1H), 2.29 (s, 3H), 2.13 (m, 1H), 1.87 (m, 1H), 1.70 (m, 2H), 1.56 (m, 1H), 1.39 (s, 9H), 1.28 (m, 3H). $^{13}$C NMR (125 MHz, d$_6$-DMSO) δ 167.4, 153.9, 145.6, 138.0, 137.6, 128.2, 128.4, 128.0, 127.6, 125.5, 78.7, 75.9, 56.9, 53.1, 46.0, 45.5, 41.9 (br), 31.0 (br), 28.1, 25.8, 25.5, 20.8.

Step 4 Benzyl Urea Intermediate

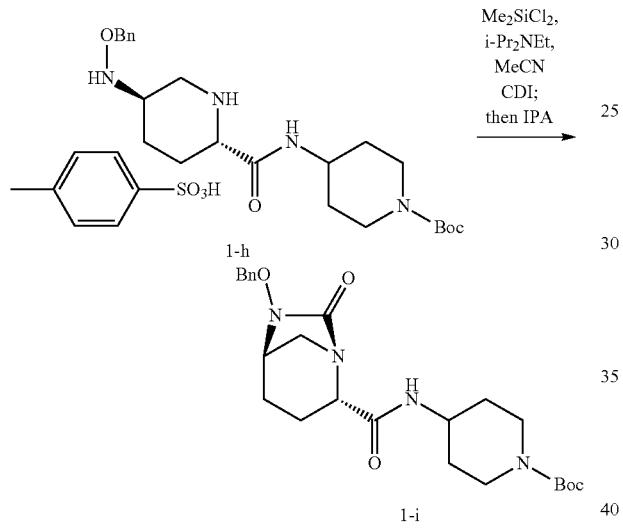

A mixture of diamine pTSA salt, 1-h, (10.0 g, 16.54 mmol) and N,N-diisopropylethylamine (i-Pr$_2$NEt) (4.9 mL, 28.12 mmol equivalents) in acetonitrile (MeCN) (50 mL) was azeotropically dried at 50° C. in vacuum at a volume of ~30 mL. The batch was then diluted with MeCN to ~60 mL and additional i-Pr$_2$NEt (10.1 mL, 57.89 mmol) was added. The reaction mixture was cooled to 10° C. Dimethyldichlorosilane (Me$_2$SiCl$_2$) (2.8 mL, 23.16 mmol) was added dropwise, while maintaining the internal temperature at 10° C. The reaction mixture was stirred for additional 1-2 h at 10° C. Then, carbonyldiimidazole (CDI) (4.0 g, 24.81 mmol) was added at ambient temperature and the batch was stirred at 45° C. until the reaction was deemed completed. IPA (5.1 mL, 66.16 mmol) was then added dropwise at 45° C. The batch was agitated at 45° C. until the reaction was deemed completed. Toluene (50 mL) followed by 2M HCl (40 mL) was then added dropwise, while maintaining the temperature at 5° C. The separated organic phase was washed with 2M HCl (40 mL) followed by 5 wt % sodium bicarbonate (NaHCO$_3$) (20 mL). Activated carbon (3.0 g) was charged to the organic layer. The mixture was agitated at 55° C. and then cooled to ambient temperature. The filtrate was concentrated to approximately 30 mL at 45° C., and the batch was seeded with benzyl urea seeds. Heptane (82 mL) was added at 45° C. over several hours. The slurry was then cooled to 10° C. before filtration. The wet cake was washed with a solution of 20% toluene in heptane (20 mL). Vacuum oven drying at less than about 60° C. gave the desired product, 1-i. NMR data matched those previously reported [WO 2016 089718A1].

Step 5 Hydrogenolysis

Tert-butyl 4-((1R,2S,5R)-6-hydroxy-7-oxo-1,6-diazabicyclo[3.2.1]octane-2-carboxamido)piperidine-1-carboxylate (1-j)

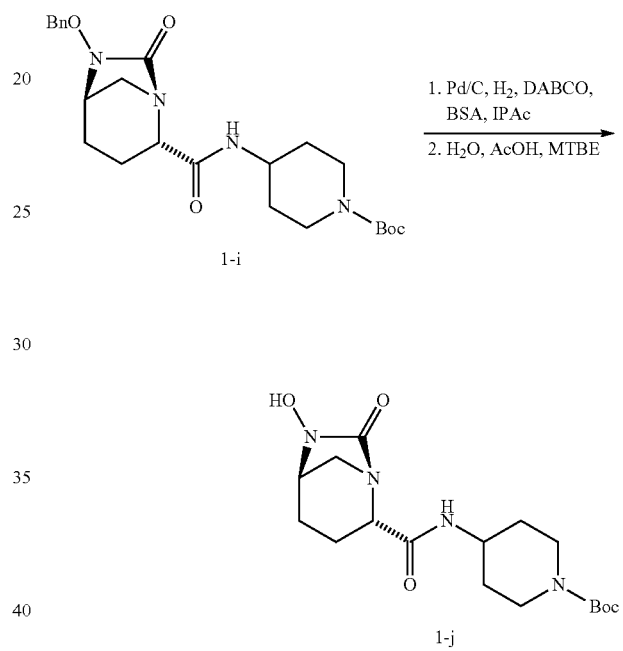

Palladium on carbon (Pd/C) (5%, 50% water wet, 4.6 g) was azeotropically dried with isopropyl acetate (IPAc) at a final volume of about 550 mL. Benzyl urea (458.6 g, 0.1 mol), N,O-bis(trimethylsilyl)acetamide (95%, 32.2 mL, 0.125 mol), and 1,4-diazabicyclo[2.2.2]octane (DABCO) (0.224 g, 0.002 mol) were added to the catalyst and IPAc mixture. The batch was hydrogenated at 50 psig and 20° C. until the reaction was complete. The catalyst was filtered and washed with IPAc (275 mL). The combined filtrate was concentrated under reduced pressure at a final volume of about 640 mL. A portion of a solution of acetic acid (5.4 g, 0.07 mol) and water (4.7 g, 0.26 mol) was combined with a portion of the batch solution and seeded with hydroxyl urea. The remaining batch solution and the aqueous acetic acid solution were mixed and aged for several hours. Methyl tert-butyl ethyl (MTBE) (275 mL) was added and the mixture was subsequently cooled to 15-20° C. The batch was then filtered and the wet cake was washed with a solution of 20% MTBE in IPAc (140 mL). Vacuum oven dry at 40° C. gave the 1-j. NMR data matched those previously reported in international application published as WO2018/053057.

Step 6 Sulfation

Tetra-butylammonium (1R,2S,5R)-2-((1-(tert-butoxycarbonyl)piperidin-4-yl)carbamoyl)-7-oxo-1,6-diazabicyclo[3.2.1]octan-6-yl Sulfate (1-k)

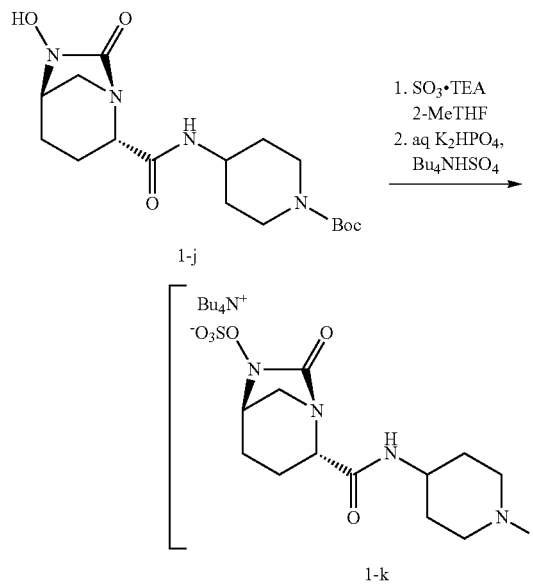

A mixture of hydroxy urea, 1-j, (10.0 g, 27.1 mmol) and SO$_3$·TEA (7.4 g, 40.7 mmol) in 2-methyltetrahydrofuran (2-MeTHF) (100 mL) was agitated at 38° C. until the reaction was complete. The batch was then cooled to ambient temperature. A solution of dipotassium phosphate (K$_2$HPO$_4$) (8.5 g, 48.9 mol) in water (130 mL) was added. Tetrabutylammonium hydrogensulfate (Bu$_4$NHSO$_4$) (10.1 g, 29.9 mmol) was then charged over 2 h and the biphasic mixture was stirred for ≥0.5 h. The organic phase was separated out and the aqueous phase was extracted with 2-MeTHF (60 mL). The combined organic phase was washed with aqueous sodium chloride solution (20 wt %, 50 mL). The organic phase was azeotropically solvent switched to acetonitrile at a volume of ≥50 mL. The batch was treated with activated carbon (≥1 g). The batch was filtered and the filtrate containing compound 1-k, was azeotropically concentrated and directly used "as is" for the subsequent Step 5.

Step 5 Boc Deprotection

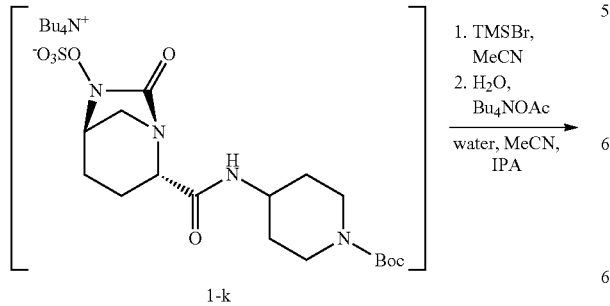

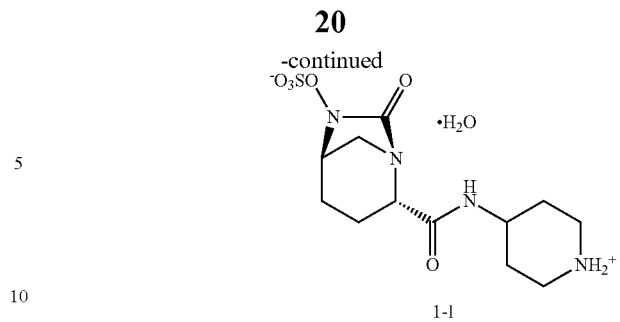

To a solution of Boc sulfate, 1-k, (11.17 mmol, 5.0 g assay of the sulfate anion) in MeCN (50 mL) was added trimethylsilyl bromide (TMSBr) (15.08 mmol, 2.31 g) at ambient temperature. The reaction mixture was agitated overnight. A solution of tetrabutylammonium acetate-acetic acid complex (2.79 mmol, 1.09 g) in MeCN (5.0 mL), and water (6.0 mL) was added over 1 h. After aging the mixture for several hours, IPA (30 mL) was subsequently added over 3 h. The batch was agitated for 2-24 h before filtration. The wet cake was washed with of IPA/water (90:10) solution (15 mL×2). Dry suction gave the desired product, 1-1. NMR data matched those previously reported. (See for example, Miller S. P. et al., "Practical and Cost-Effective Manufacturing Route for the Synthesis of a β-Lactamase Inhibitor". *Organic Letters* 2014 16 (1), 174-177).

While the foregoing specification teaches the principles of the present invention, with examples provided for the purpose of illustration, the practice of the invention encompasses all of the usual variations, adaptations and/or modifications that come within the scope of the following claims.

What is claimed is:

1. A process for preparing a compound of Formula I or a salt thereof

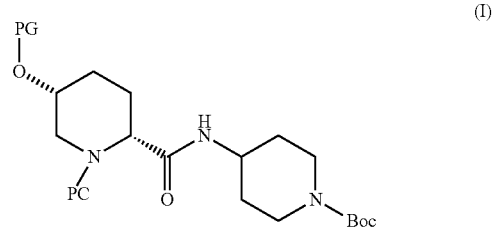

comprising:
  A) coupling a pipecolic acid with an azacycloalkylamine in the presence of a first organic solvent, N-(3-dimethylaminopropyl)-N'-ethylcarbodiimide hydrochloride (EDC), 1-hydroxy-2-pyridone (HOPO), and at least one acid to form a compound of formula II

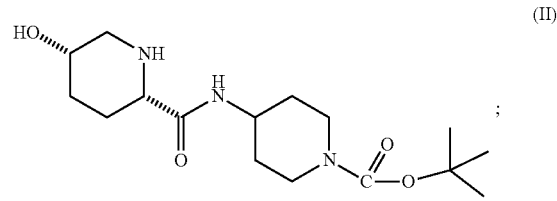 [SMILES: CC(C)(C)OC(=O)N1CCC(NC(=O)[C@@H]2CC[C@H](O)CN2)CC1 ; ";"]

and

B) contacting the compound of formula (II) with a protecting group in the presence of a nucleophilic catalyst and a second organic solvent to form the compound of formula I.

2. The process of claim 1, wherein in step A) the pipecolic acid is

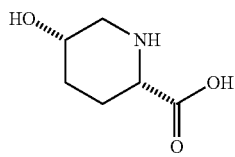

(A1)

and the azacycloalkylamine is

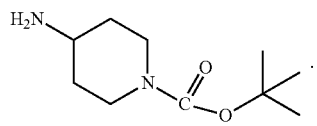

(A2)

3. The process of claim 2, wherein in step A), the at least one acid is selected from aqueous hydrochloric acid or methanesulfonic acid (MsOH).

4. The process of claim 2, wherein the first organic solvent is selected from DCM, DMF, AcNMe₂, THF, MeTHF, EtOAc, i-PrOAc and acetonitrile and mixtures thereof.

5. The process of claim 2, wherein the second organic solvent is selected from DCM, DMF, AcNMe₂, THF, MeTHF, EtOAc, i-PrOAc and acetonitrile and mixtures thereof.

6. The process of claim 4 or 5, wherein the first and second organic solvent is acetonitrile.

7. The process of claim 1, wherein the nucleophilic catalyst is 4-dimethylaminopyridine (DMAP).

8. The process of claim 7, wherein the protecting group is chosen from methanesulfonyl chloride, chloromethanesulfonyl chloride, dicloromethanesulfonyl chloride, benzenesulfonyl chloride, p-trifluromethylbenzenesulfonyl chloride, p-toluenesulfonyl chloride, p-bromobenzenesulfonyl chloride, p-fluorobenzenesulfonyl chloride, p-methoxybenzenesulfonyl chloride, 2-nitrobenzenesulfonyl chloride, 4-nitrobenzenesulfonyl chloride, 2,4-dichlorobenzenesulfonyl chloride, and p-trifluoromethylbenzenesulfonyl chloride.

9. The process of claim 8, wherein the protecting group is 2-nitrobenzenesulfonyl chloride or 4-nitrobenzenesulfonyl chloride.

10. The process of claim 9, wherein the compound of Formula (I) is

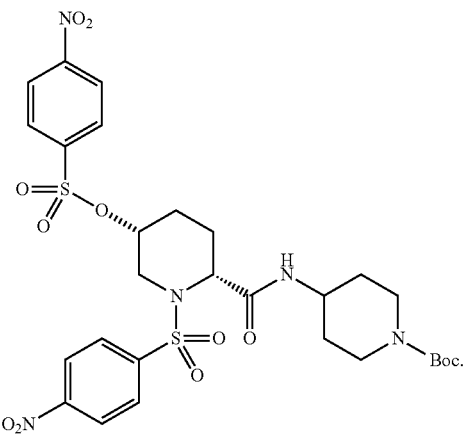 [SMILES: CC(C)(C)OC(=O)N1CCC(NC(=O)[C@H]2CC[C@@H](OS(=O)(=O)c3ccc([N+](=O)[O-])cc3)CN2S(=O)(=O)c2ccc([N+](=O)[O-])cc2)CC1]

11. A process for preparing a compound of Formula IV or a pharmaceutically acceptable salt thereof:

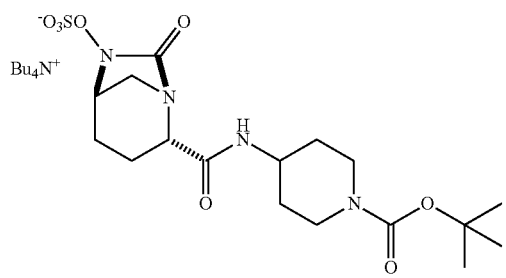

comprising:

contacting a hydroxy urea of formula (III);

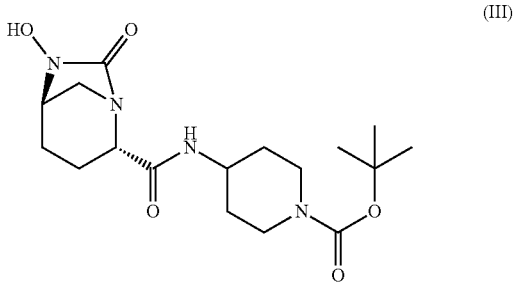 [SMILES: CC(C)(C)OC(=O)N1CCC(NC(=O)[C@@H]2CC[C@@H]3CN2C(=O)N3O)CC1]

in the presence of a sulfur trioxide amine selected from sulfur trioxide-triethyl amine, sulfur trioxide-tripropyl amine, and sulfur trioxide-tributylamine, and at least one solvent selected from 2-methyltetrahydrofuran and tetrahydrofuran to form a reaction mixture;

adding an aqueous solution of dipotassium phosphate to the reaction mixture; and adding tetrabutylammonium hydrogensulfate to form a compound (IV) in a biphasic mixture.

12. The process of claim 11 further comprising formation of the compound of formula (V)

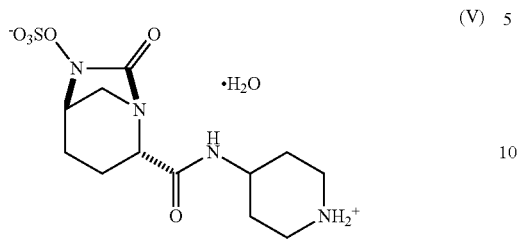

(V)

comprising:
contacting compound (IV) with trimethylsilyl bromide (TMSBr) in the presence of an organic solvent; and
adding tetrabutylammonium acetate-acetic acid complex in acetonitrile and water to form compound (V).

13. The process of claim 12, further comprising adding isopropyl alcohol to the reaction mixture containing compound (V) and filtering the resultant mixture.

* * * * *